United States Patent
Liu et al.

(10) Patent No.: US 11,821,876 B2
(45) Date of Patent: Nov. 21, 2023

(54) TEST METHOD OF MEDIUM TRANSMISSION TEST DEVICE FOR CONCRETE UNDER TEMPERATURE-OSMOTIC PRESSURE-LOAD COUPLING EFFECT

(71) Applicant: SOUTHEAST UNIVERSITY, Nanjing (CN)

(72) Inventors: Zhiyong Liu, Nanjing (CN); Xizhi Xia, Nanjing (CN); Jinyang Jiang, Nanjing (CN); Yunsheng Zhang, Nanjing (CN)

(73) Assignee: SOUTHEAST UNIVERSITY, Nanjing (CN)

(*) Notice: Subject to any disclaimer, the term of this patent is extended or adjusted under 35 U.S.C. 154(b) by 0 days.

(21) Appl. No.: 17/907,888

(22) PCT Filed: Mar. 9, 2022

(86) PCT No.: PCT/CN2022/079870
§ 371 (c)(1),
(2) Date: Aug. 29, 2022

(87) PCT Pub. No.: WO2022/206318
PCT Pub. Date: Oct. 6, 2022

(65) Prior Publication Data
US 2023/0123095 A1    Apr. 20, 2023

(30) Foreign Application Priority Data

Apr. 2, 2021    (CN) .......................... 202110365426.7

(51) Int. Cl.
*G01N 3/10*    (2006.01)
*G01N 33/38*    (2006.01)

(52) U.S. Cl.
CPC ............. *G01N 3/10* (2013.01); *G01N 33/383* (2013.01); *G01N 2203/0019* (2013.01); *G01N 2203/0048* (2013.01)

(58) Field of Classification Search
CPC .................. G01N 3/10; G01N 33/383; G01N 2203/0019; G01N 2203/0048
See application file for complete search history.

(56) References Cited

FOREIGN PATENT DOCUMENTS

| CN | 102564916 A | 7/2012 |
|----|-------------|--------|
| CN | 103364313 A | 10/2013 |

(Continued)

*Primary Examiner* — Jonathan M Dunlap
(74) *Attorney, Agent, or Firm* — Muncy, Geissler, Olds & Lowe, P.C.

(57) ABSTRACT

The present disclosure discloses a medium transmission test device and a method for concrete under a temperature-osmotic pressure-load coupling effect. The device includes a loading device and a water pressurization device; the loading device includes a press, an upper steel plate and a lower steel plate used for clamping a test block, and a fastener that connects the upper and lower steel plates; the upper steel plate includes a first steel plate and a second steel plate; a spring is sleeved on a screw between the first steel plate and the second steel plate; the water pressurization device includes a liquid storage tank, a pressurization pump, a liquid storage pool, a connecting pipe for communicating the pressurization pump to the liquid storage tank, and a connecting pipe for connecting the pressurization pump to the liquid storage pool; the liquid storage tank is provided with an open end; and a tank port of the open end is fixedly connected to a side surface of the test block. The present disclosure achieves a load-temperature-osmotic pressure coupling effect on concrete, can well simulate a complicated severe environment where underground concrete is located, and provides an effective device support for the study of the durability of concrete under complicated severe conditions.

1 Claim, 8 Drawing Sheets

(56) References Cited

FOREIGN PATENT DOCUMENTS

| | | | |
|---|---|---|---|
| CN | 107543755 A | 1/2018 | |
| CN | 108918250 A | 11/2018 | |
| CN | 109655380 A | 4/2019 | |
| CN | 110132741 A | 8/2019 | |
| CN | 110455699 A | 11/2019 | |
| CN | 110595975 A | 12/2019 | |
| CN | 210665327 U | 6/2020 | |
| CN | 111896446 A | 11/2020 | |
| CN | 111896454 A | 11/2020 | |
| CN | 113109159 A | 7/2021 | |
| CN | 109507097 B * | 8/2022 | ............ G01N 17/00 |
| KR | 101966694 | 4/2019 | |

* cited by examiner

TEST METHOD OF MEDIUM TRANSMISSION TEST DEVICE FOR CONCRETE UNDER TEMPERATURE-OSMOTIC PRESSURE-LOAD COUPLING EFFECT

TECHNICAL FIELD

The present disclosure relates to a concrete performance test device, in particular to test method of a test device for medium transmission performance of concrete.

BACKGROUND

Cement concrete is currently the most widely used building material in the largest use amount in the field of civil engineering. Concrete is considered to be a building material with extremely high durability. However, with its applications in complex engineering environments, a premature failure of a concrete structure due to the durability problem has attracted the attention of civil engineering scholars.

Concrete is often subjected to a coupling effect of a mechanical factor (a static load, a dynamic load) and an environmental factor (chloride ion erosion, carbonization, a freeze-thaw cycle, sulfate erosion, a temperature, etc.) during service, resulting in premature deterioration and early withdrawal from service of structural concrete. In some special environments, such as in an underground space structures and an underwater structure, concrete will be subjected to separate effects or a combined effect of an osmotic pressure, a load and a temperature, thus affecting a transmission behavior of an erosion medium inside the concrete and further affecting the durability of the concrete.

At present, there are many devices used to study the transmission performance of concrete under separate effects of an osmotic pressure and a load, but there are few devices that can achieve a coupling effect of an osmotic pressure and a load. Therefore, it is necessary to design a device that can achieve a coupling effect of an osmotic pressure and a load.

SUMMARY

Purposes of the disclosure: For the shortcomings of a current device for the transmission performance of concrete under effects of an osmotic pressure and a load, a first purpose of the present disclosure is to provide a test method of a medium transmission test device for concrete under a temperature-osmotic pressure-load coupling effect, which can achieve a medium transmission test under the temperature-osmotic pressure-load coupling effect.

Technical solutions: The present disclosure discloses a test method of a medium transmission test device for concrete under a temperature-osmotic pressure-load coupling effect. The test device includes a loading device and a water pressurization device; the loading device includes a press, an upper steel plate and a lower steel plate used for clamping a test block, and a fastener that connects the upper and lower steel plates; the upper steel plate includes a first steel plate and a second steel plate; a spring is sleeved on a screw between the first steel plate and the second steel plate; the water pressurization device includes a liquid storage tank, a pressurization pump, a liquid storage pool, a connecting pipe for communicating the pressurization pump to the liquid storage tank, and a connecting pipe for connecting the pressurization pump to the liquid storage pool; the liquid storage tank is provided with an open end; and a tank port of the open end is fixedly connected to a side surface of the test block, so as to achieve hermetical connection between the tank port of the liquid storage tank and the side surface of the test block. The test device also includes a high-low temperature test chamber in which a space for placing the loading device and the liquid storage tank is provided; and a through hole for allowing the connecting pipe to pass through is formed in the test chamber. That is, the loading device is used for applying a required load to the test block. After the load is applied to the steel plates, the press transmits a force to the test block via the steel plates and a spring/disc spring; the side surface of the test block is hermetically connected to the tank port of the open end; the liquid storage tank is filled with a test solution; a water pressure is applied to the test block through the pressurization pump; the loading device and the water pressurization device are placed in the high-low temperature alternating damp heat test chamber; a temperature is controlled by the test chamber; and finally an osmotic pressure-load-temperature coupling effect is achieved on the test block. The water pressurization device also includes a trough type connecting plate used for fixing the test block; the trough type connecting plate is fixedly connected to the open end; and a sealing pad is arranged at a joint of the test block and the tank port. The tank port of the liquid storage tank may be set according to an actual test requirement. Optionally, there are one or more tank ports. Preferably, the liquid storage tank has two open ends which are respectively located at left and right ends of the liquid storage tank. The type of the spring/disc spring is selected according to an actual situation. A nut and a screw adopt a high strength screw and a high strength nut.

The test method includes the following steps:
(1) placing the test block between the upper steel plate and the lower steel plate; applying, by the press, a pressure to the steel plates according to a required load value; connecting the steel plates by the fastener; tightening the fastener to maintain the pressure, thus forming a loading assembly; and placing the test block in a center position between the upper steel plate and the lower steel plate, so that the load is uniform;
(2) placing the loading assembly at the tank port of the open end of the liquid storage tank; fixedly connecting the side surface of the test block to the tank port to block the tank port by the test block; filling the liquid storage tank with a test solution; communicating one end of the connecting pipe to the liquid storage tank and communicating the other end to the pressurization pump, so as to connect the loading assembly to the water pressurization device; arranging the loading assembly and the liquid storage tank in the high-low temperature test chamber; and passing the connecting pipe through the test chamber to be communicated to the pressurization pump; and
(3) pressurizing the test solution through the pressurization pump, so as to apply an osmotic pressure to the test block, where a pressurization range of the pressurization pump is 0-10 MPa. A temperature range of the high-low temperature test chamber is −15° C.-200° C. The test solution may be water, NaCl, $NaSO_4$, and the like.

Specifically, a test process is as follows:
(1) In order to prevent the influence on a sealing effect because an epoxy resin sealing layer of the test block cracks in the loading process, loading is performed before sealing.

The loading device is assembled, and the test block is placed in a center of a bottom plate; the loading device is put on a lower pressure bearing plate of an electro-hydraulic servo press; a load parameter and sufficient pressure holding time are set according to a required load; and after the press reaches a set load, a wrench is used to tighten the nut within the pressure holding time period, so as to achieve pressure maintenance.
  (2) The loading assembly is removed, and all surfaces except the one in contact with the solution are sealed with epoxy resin.
  (3) The test block is placed in a U-shaped groove of the trough type connecting plate and is encircled by the trough type connecting plate; a clearance between the test block and the U-shaped groove is filled with a silica gel pad; a silica gel ring is adhered to a test block contact surface using epoxy resin, and the other surface of the silica gel ring is adhered to the liquid storage tank; the liquid storage tank is connected to the trough type connecting plate by a bolt, and the bolt is then tightened.
  (4) After the epoxy resin is coagulated, a whole composed of the loading assembly and the liquid storage tank is put into the high-low temperature alternating damp heat test chamber.
  (5) The liquid storage tank is filled with the test solution; one end of a high-pressure connecting pipe is connected to a joint of the liquid storage tank, and the other end passes through the through hole in the high-low temperature alternating damp heat test chamber and is connected to the electric pressurization pump outside the chamber; and the two joints are sealed by sealing rings or sealing tapes.
  (6) One end of the connecting pipe is connected to the electric pressurization pump, and the other end is put into the liquid storage pool; and the liquid storage pool is filled with a proper amount of the test solution.
  (7) The high-low temperature alternating damp heat test chamber is turned on; and a test temperature is set through a control panel.
  (8) The electric pressurization pump is turned on; a pressure adjustment knob is rotated; when a reading on a pressure gauge reaches a pressure for a test, the knob is locked, and the switch is turned off to maintain the pressure and start a transmission test.

To design this device, many technical obstacles need to be overcome: 1. The size of the device shall be strictly controlled. First, the device needs to adapt to spaces of the high-low temperature alternating damp heat test chamber and the electro-hydraulic servo press. Second, the device shall meet a test requirement of a high water pressure. The space of the liquid storage container shall not be too large, or it is difficult for pressurization. Finally, an osmosis device and the loading device can be effectively combined and are easy to disassemble. Therefore, according to the above-mentioned requirements, the osmosis device and the loading device with reasonable sizes are designed. 2. A high requirement is put forward to the sealing property. The device is used for studying a transmission test, so the device is required to have extremely high leakproofness due to a long study cycle. In addition, due to a high water pressure, the device is also required to have high sealing property. Therefore, joints between pipelines as well as between the pipelines and the liquid storage container are sealed by sealing tapes and sealing rings; the silica gel pad is arranged between the liquid storage container and a test piece; the silica gel pad, the liquid storage container and the test piece are adhered by epoxy resin; and the liquid storage container and the trough type connecting plate are connected by four bolts. Therefore, in a breakthrough, the present disclosure achieves a load-temperature-osmotic pressure coupling effect on concrete, can well simulate a complicated severe environment where underground concrete is located, and provides an effective device support for the study of the durability of concrete under complicated severe conditions.

Beneficial effects: The present disclosure provides a test method of a device for coupling effects of an osmotic pressure and a pressure load. The osmosis device and the loading device are combined, so that separate effects or a coupling effect of a load and an osmotic pressure can be achieved. The device can be put into the high-low temperature alternating damp heat test chamber since it has a small size and a simple structure and is convenient to move, thus achieving separate effects of a load, a temperature and an osmotic pressure, coupling effects of every two of a load, a temperature and an osmotic pressure, and even a coupling effect of a load, a temperature and an osmotic pressure. In addition, the device can also be put into a carbonation tank or other instruments to study mutual coupling effects of carbonization, a load, an osmotic pressure, salt erosion and the like. Therefore, this device and this test method provide an effective device support and a test method for the study of the durability of concrete under complicated severe conditions.

DETAILED DESCRIPTION

The present disclosure is further described in detail below in combination with examples.

Figure 1:
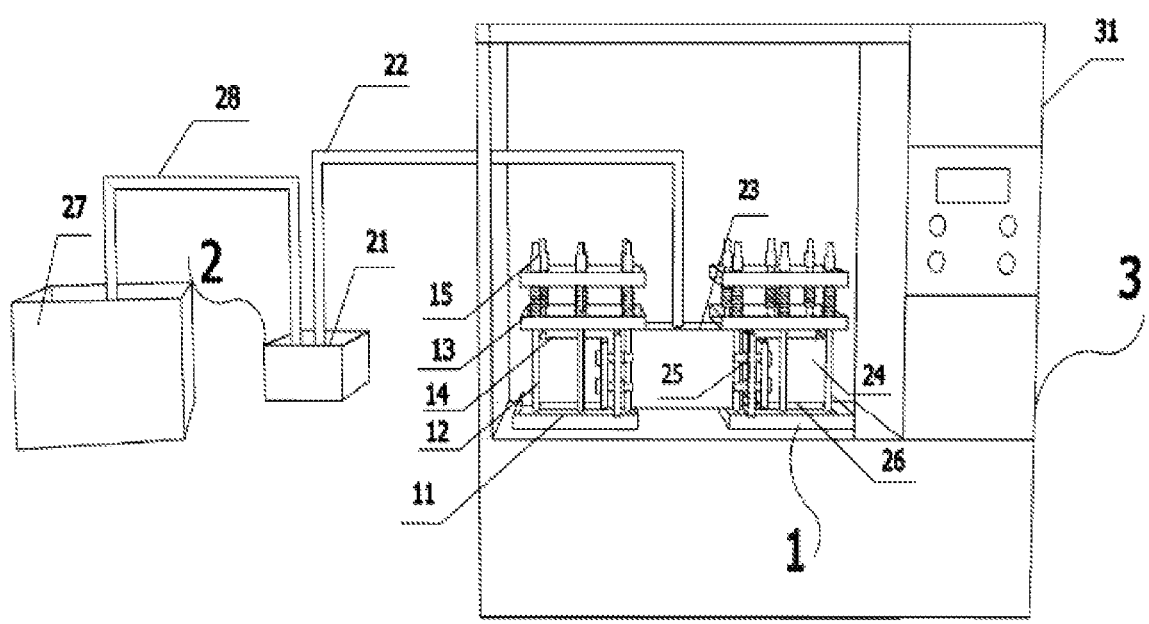
FIG. 1 is a schematic structural diagram of a test device of the present disclosure.

FIG. 1 illustrates a schematic structural diagram of a medium transmission test device for concrete of the present disclosure. The test device is a water/ion transmission test device under a load-temperature-osmotic pressure coupling effect, and includes a loading device 1, a water pressurization device 2 and a temperature test chamber 3.

The temperature test chamber 3 in this example is a high-low temperature alternating damp heat chamber 31. There is a large enough space inside the high-low temperature alternating damp heat chamber 31, so that the loading device 1 and the water pressurization device 2 can be put into the high-low temperature alternating damp heat chamber.

Figure 2:
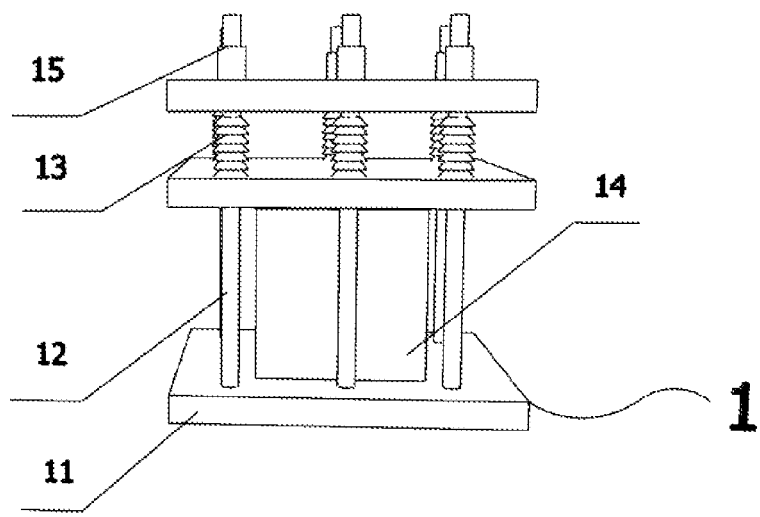
FIG. 2 is a schematic structural diagram of a loading module.

As shown in FIG. 2, the loading device 1 includes an electro-hydraulic servo press (not shown), a steel plate 11 used for clamping a test block, and several fasteners for connecting the steel plate. The steel plate 11 includes an upper steel plate and a lower steel plate. The upper steel plate includes a first steel plate and a second steel plate located above the first steel plate. A spring/disc spring 13 is sleeved on a screw between the first steel plate and the second steel plate. The fasteners in this example achieve fastening by cooperation between screws and nuts. That is, three steel plates with connecting holes, six screws, six nuts and a proper number of springs/disc springs are used. The type of the spring/disc spring can be selected according to a requirement. The bolts adopt high strength bolts. The steel plates are stainless steel. Six connecting holes are uniformly distributed on left and right sides of the steel plates. Six screws pass through the connecting holes to meet a requirement for a higher load. A test block 14 is placed in a center position of the lower steel plate. The three steel plates 11 are placed in parallel along a horizontal direction and are connected in series together through the six screws 12 that are vertically disposed. The spring/disc spring 13 is sleeved on the screws 12 between the two upper steel plates 11 (i.e., the first steel plate and the second steel plate). Nuts 15 are screwed at top ends of the screws 12. During use, the test block can be fixed and subjected to pressure maintenance by means of screwing the nuts at the tops.

Figure 3:
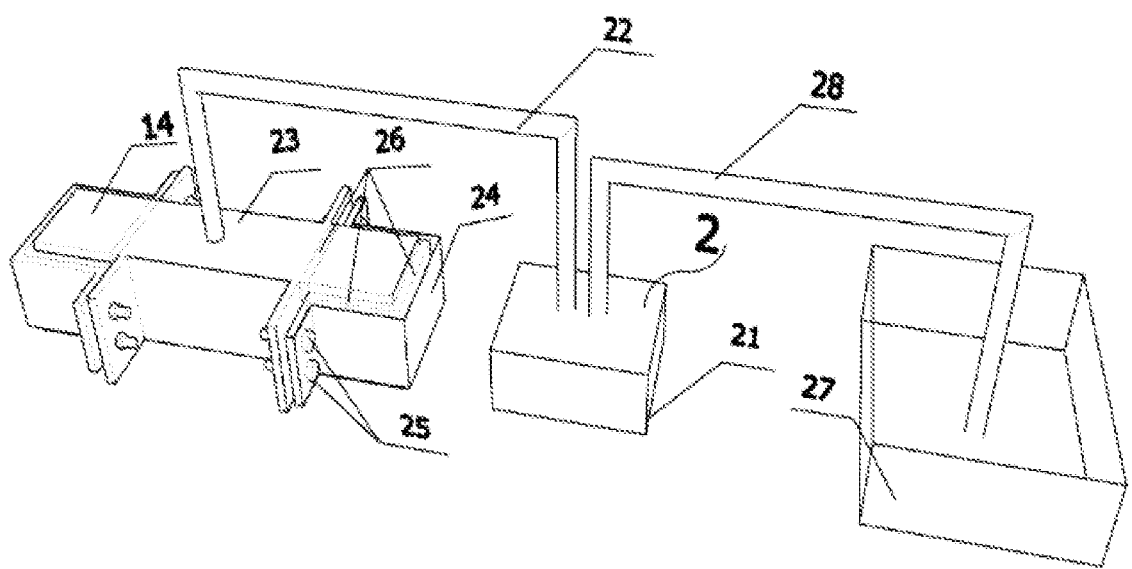
FIG. 3 is a schematic structural diagram of a water pressurization module.

As shown in FIG. 3, the water pressurization device 2 includes a liquid storage tank 23, an electric pressurization pump 21, a high-pressure connecting pipe 22, a liquid storage pool 27, a water inlet pipe 28, a trough type connecting plate 24 used for fixing the test block, a bolt 25, and a silica gel pad (ring) 26. The high-pressure connecting pipe 22 is used for communicating the pressurization pump 21 to the liquid storage tank 23. One end of the connecting pipe 22 is communicated to the liquid storage tank 23, and the other end is communicated to the pressurization pump 21. A through hole for allowing the connecting pipe to pass is formed in a side wall of the high-low temperature alternating damp heat chamber 31. The high-pressure connecting pipe 22 connects the electric pressurization pump 21 to the liquid storage container 23 through the through hole in the high-low temperature alternating damp heat chamber 31. A tank body of the liquid storage tank 23 is a hollow cuboid. A through hole communicated to the high-pressure connecting pipe 22 is formed in a top of the tank body. Left and right ends of the tank body are provided with openings to respectively form a left tank port and a right tank port. Loading assemblies are arranged on two sides of the left tank port and the right tank port.

Figure 4:
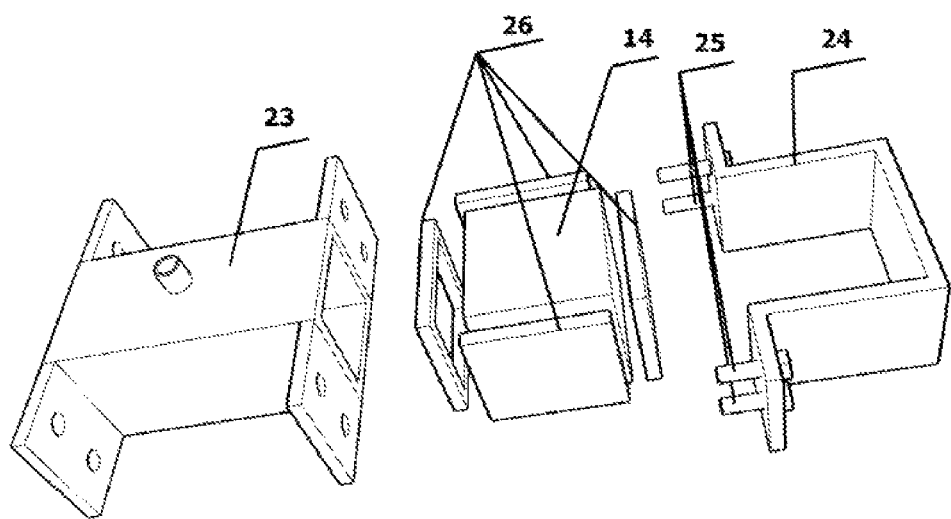
FIG. 4 is a schematic detailed diagram of a water pressurization module.

As shown in FIG. 4, connection to the right tank port of the liquid storage tank 23 is taken as an example. The right tank port extends towards an outer side to form two connecting plates. The test block 14 is put into a groove in the trough type connecting plate 24, and a clearance between the test block and the groove is filled with the silica gel pad 26. The connecting plate outwards extending from the right tank port of the liquid storage tank 23 is fixedly connected to the trough type connecting plate 24 through the bolt 25. The right tank port of the liquid storage tank is hermetically connected to a left side surface of the test block 14 through the silica gel ring 26. The above steel plate, the liquid storage tank and the connecting plate are all stainless steel.

The present disclosure provides a device for studying a transmission test of a medium such as water/ions in concrete under a temperature-osmotic pressure-load coupling effect. In a test, the test block 14 is placed on the loading device. A required load is applied through an electro-hydraulic servo press. A wrench is used to tighten the nut to maintain the pressure. The liquid storage tank is connected to the loading device and is placed in the high-low temperature alternating damp heat test chamber, and a temperature is controlled by the test chamber. The liquid storage container is filled with a solution. A high-pressure water inlet pipe is connected to the electric pressurization pump through a hole in the test chamber. A water pressure is applied through the pressurization pump.

Specifically, a test process can be carried out according to the following steps:

(1) In order to prevent the influence on a sealing effect because an epoxy resin sealing layer of the test block cracks in the loading process, loading is performed before sealing.

The loading device is assembled. The test block is placed in a center position of the lower steel plate. The upper steel plates are arranged above the test block. The steel plates are connected in sequence by the screws. The high strength bolts are screwed into the tops of the screws.

The loading device is put on a lower pressure bearing plate of the electro-hydraulic servo press. A load value and long enough pressure maintenance time are set according to a set stress ratio. After the press reaches the set load, the wrench is used to tighten the nuts within the time period of pressure holding, so as to achieve pressure maintenance, thus forming a loading assembly.

(2) The loading assembly is removed from the press. At this time, upper and lower surfaces of the test block are both in tight contact with the steel plates. The other three side surfaces of the test block except the one in contact with the solution are all sealed with epoxy resin.

(3) The test block is encircled by the trough type connecting plate, and the test block is located in the groove of the trough type connecting plate. The clearance between the test block and the trough type connecting plate is filled with the silica gel pad having a thickness of 10 mm.

A silica gel ring having a width of 10 mm is adhered by the epoxy resin to each tank port and a test block contact surface, and the other surface of the silica gel ring is adhered to the tank port of the liquid storage tank. The connecting plate outwards extending from the tank port is connected to the trough type connecting plate by the bolt, and the bolt is then tightened.

(4) After the epoxy resin is coagulated, a whole composed of the loading assembly and the liquid storage container is put into the high-low temperature alternating damp heat test chamber.

(5) The liquid storage tank is filled with NaCl solution with a concentration of 10%. One end of the high-pressure connecting pipe is connected to a joint at the top of the liquid storage tank, and the other end passes through the through hole in the high-low temperature alternating damp heat test chamber and is connected to the electric pressurization pump. The two joints are sealed by sealing rings and sealing tapes.

(6) One end of the water inlet pipe is put into the liquid storage pool, and the other end is connected to the pressurization pump. A proper amount of NaCl solution with the concentration of 10% is injected into the liquid storage pool.

(7) The high-low temperature alternating damp heat test chamber is turned on. A required temperature is set through a control panel.

(8) The electric pressurization pump is turned on. A pressure adjustment knob is rotated. When a reading on a pressure gauge reaches a required water pressure, the knob is locked, and the switch is turned off to maintain the pressure and start a transmission test.

Example 1

In this example, a concrete sample with a water-glue ratio of 0.16 and ultra-high performance is adopted, which has a dimension of 100 mm×100 mm×100 mm. The cubic test block is taken out after steam curing for 3 d. In an application case, an experimental solution is NaCl solution with a concentration of 10%, an experimental temperature is 30° C., an osmotic pressure is 4 MPa, and a stress ratio adopts 0.3 (a ratio of a required stress to the strength of the concrete.)

Example 2

In this example, a concrete sample with a water-glue ratio of 0.16 and ultra-high performance is adopted, which has a dimension of 100 mm×100 mm×100 mm. The cubic test block is taken out after steam curing for 3 d. In an application case, an experimental solution is NaCl solution with a concentration of 10%, an experimental temperature is 70° C., an osmotic pressure is 4 MPa, and a stress ratio adopts 0.3.

Example 3

In this example, a concrete sample with a water-glue ratio of 0.16 and ultra-high performance is adopted, which has a dimension of 100 mm× 100 mm× 100 mm. The cubic test block is taken out after steam curing for 3 d. In an application case, an experimental solution is NaCl solution with a concentration of 10%, an experimental temperature is 30° C., an osmotic pressure is 2 MPa, and a stress ratio adopts 0.3.

Figure 5:
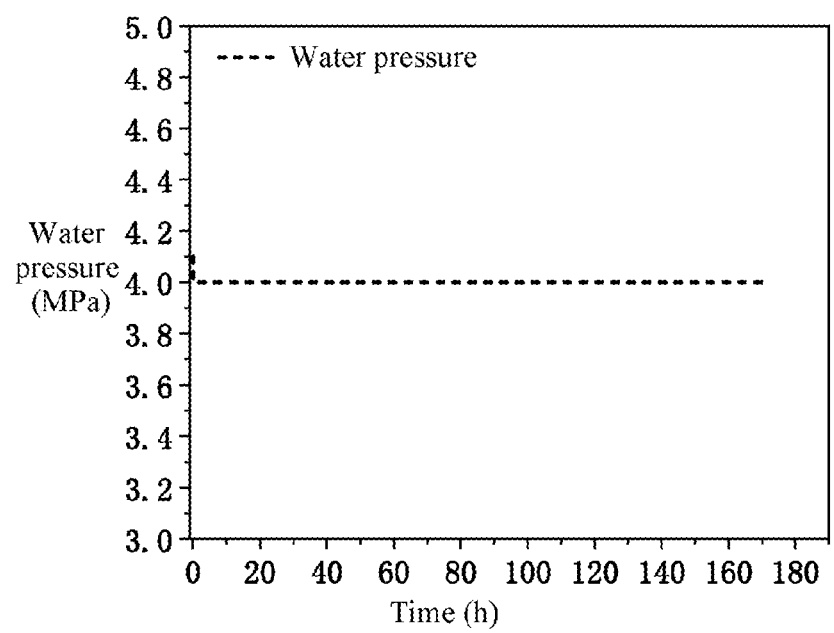
FIG. 5 is a curve where a water pressure changes over time.
Figure 6:
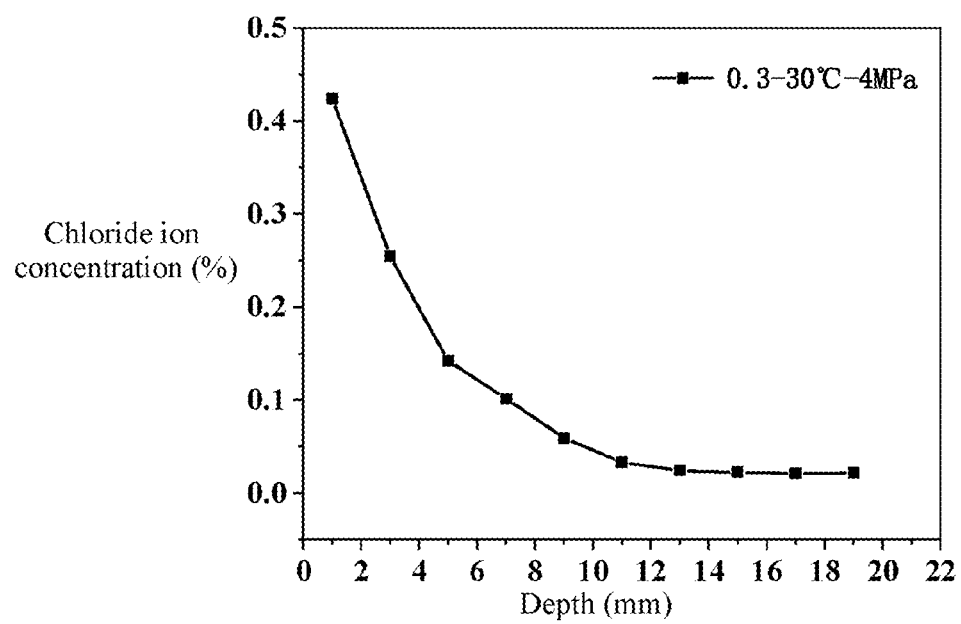
FIG. 6 is a curve of a chloride ion concentration distribution of concrete under a coupling effect of a stress ratio of 0.3, 30° C. and an osmotic pressure of 4 MPa for 3 days.
Figure 7:
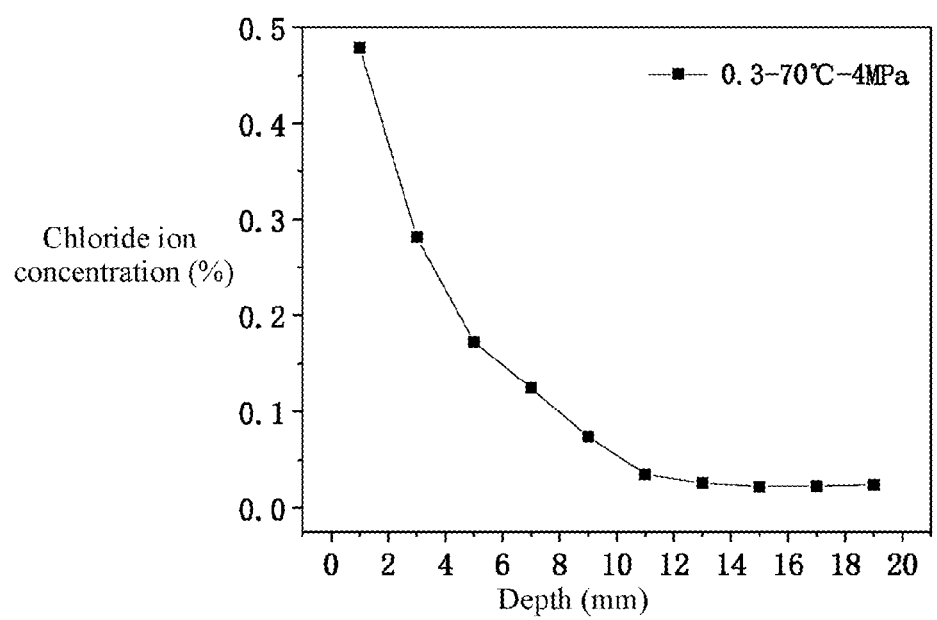
FIG. 7 is a curve of a chloride ion concentration distribution of concrete under a coupling effect of a stress ratio of 0.3, 70° C. and an osmotic pressure of 4 MPa for 3 days.
Figure 8:
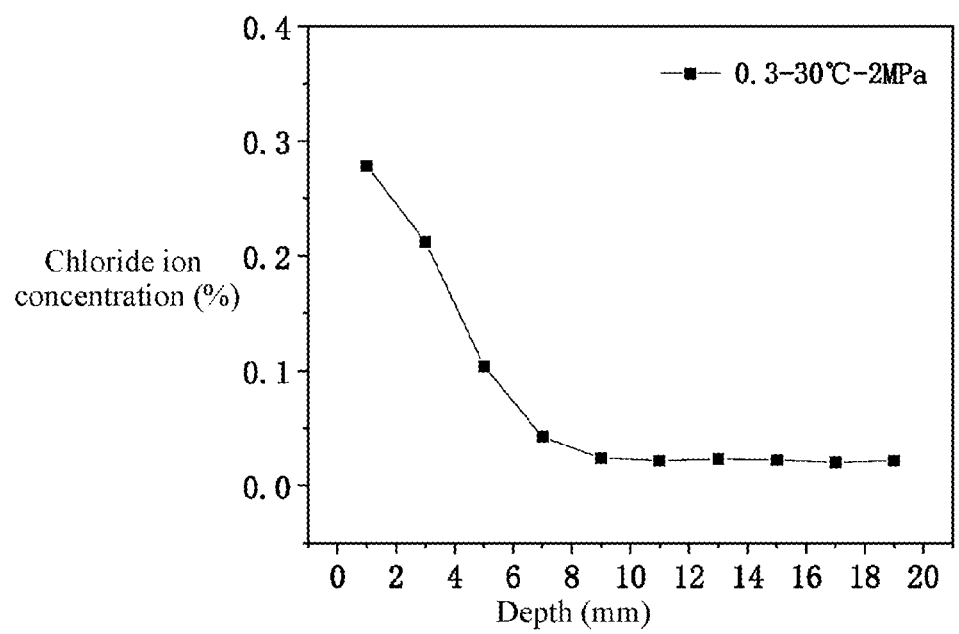
FIG. 8 is a curve of a chloride ion concentration distribution of concrete under a coupling effect of a stress ratio of 0.3, 30° C. and an osmotic pressure of 2 MPa for 3 days.

FIG. 5 is a curve where a water pressure changes over time. It can be seen that after it lasts for 7 days, the water pressure is basically kept unchanged, indicating that the device has extremely good leakproofness. FIG. 6 to FIG. 8 are respectively curves of chloride ion concentration distribution inside the concrete obtained in the above examples 1 to 3. It can be seen that the variation trend of the chloride ion concentration is basically consistent with results obtained by similar studies, and a good regularity is shown after parameters such as temperature and osmotic pressure are changed. Therefore, it is feasible to apply this device to study a medium transmission test on concrete. In a breakthrough, the present disclosure achieves a load-temperature-osmotic pressure coupling effect on concrete, can well simulate a complicated severe environment where underground concrete is located, and provides an effective device support for the study of the durability of concrete under complicated severe conditions.

What is claimed is:

1. A test method of a medium transmission test device for concrete under a temperature-osmotic pressure-load coupling effect, wherein the test device comprises a loading device and a water pressurization device; the loading device comprises a press, an upper steel plate and a lower steel plate used for clamping a test block, and a fastener that connects the upper and lower steel plates; the upper steel plate comprises a first steel plate and a second steel plate; a spring is sleeved on a screw between the first steel plate and the second steel plate; the water pressurization device comprises a liquid storage tank, a pressurization pump, a liquid storage pool, a connecting pipe for communicating and connecting the pressurization pump to the liquid storage tank; the liquid storage tank is provided with an open end; and a tank port of the open end is fixedly connected to a side surface of the test block;

the test device also comprises a high-low temperature test chamber in which a space for placing the loading device and the liquid storage tank is provided; and a through hole for allowing the connecting pipe for communicating the pressurization pump to the liquid storage tank to pass through is formed in the test chamber;

the water pressurization device also comprises a trough type connecting plate used for fixing the test block; the trough type connecting plate is fixedly connected to the open end; and a sealing pad is arranged at a joint of the test block and the tank port;

the test method comprises the following steps:

(1) placing the test block between the upper steel plate and the lower steel plate; applying, by the press, a pressure to the steel plates according to a required load value; connecting the steel plates by the fastener; tightening the fastener to maintain the pressure, thus forming a loading assembly; and placing the test block in a center position between the upper steel plate and the lower steel plate;

(2) placing the loading assembly at the tank port of the open end of the liquid storage tank; fixedly connecting the side surface of the test block to the tank port to block the tank port by the test block; filling the liquid storage tank with a test solution; communicating one end of the connecting pipe to the liquid storage tank and communicating the other end to the pressurization pump, so as to connect the loading assembly to the water pressurization device; arranging the loading assembly and the liquid storage tank in the high-low temperature test chamber, and passing the connecting pipe through the test chamber to be communicated to the pressurization pump; and maintaining a temperature range of the high-low temperature test chamber at −15° C.-200° C.;

(3) pressurizing the test solution through the pressurization pump, so as to apply an osmotic pressure to the test block; and maintaining a pressurization range of the pressurization pump at 0-10 MPa.

* * * * *